(12) United States Patent
Weese et al.

(10) Patent No.: US 9,393,079 B2
(45) Date of Patent: Jul. 19, 2016

(54) PROCESSING OF IMAGES OF INTERVENTIONAL INSTRUMENTS WITH MARKERS

(75) Inventors: Juergen Weese, Aachen (DE); Sabine Mollus, Aachen (DE); Raoul Florent, Ville d'Avray (FR); Lucile Nosjean, Rueil-Malmaison (FR); Pierre Lelong, Nogent sur Marne (FR); Peter Maria Johannes Rongen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1462 days.

(21) Appl. No.: 11/573,292

(22) PCT Filed: Jul. 21, 2005

(86) PCT No.: PCT/IB2005/052456
§ 371 (c)(1),
(2), (4) Date: Feb. 6, 2007

(87) PCT Pub. No.: WO2006/016290
PCT Pub. Date: Feb. 16, 2006

(65) Prior Publication Data
US 2009/0216111 A1 Aug. 27, 2009

(51) Int. Cl.
*A61B 5/05* (2006.01)
*A61B 19/00* (2006.01)
(52) U.S. Cl.
CPC ....... *A61B 19/5244* (2013.01); *A61B 2090/392* (2016.02)

(58) Field of Classification Search
CPC ................................................. A61B 2090/392
USPC .......................... 600/414, 424, 426, 427, 431
See application file for complete search history.

(56) References Cited

U.S. PATENT DOCUMENTS

| 5,944,712 | A | 8/1999 | Frassica et al. | |
| 6,574,493 | B2 * | 6/2003 | Rasche et al. | 600/407 |
| 2001/0034480 | A1 | 10/2001 | Rasche et al. | |
| 2003/0209096 | A1 | 11/2003 | Pandey et al. | |
| 2004/0138556 | A1 | 7/2004 | Cosman | |

FOREIGN PATENT DOCUMENTS

DE          10246147 A1     4/2004

* cited by examiner

*Primary Examiner* — Mark Remaly

(57) ABSTRACT

A method and an image processing system for the evaluation of projection images generated by an X-ray imaging system, wherein the images may show different instruments of a given set of interventional instruments like catheters or guide wires. The instruments are equipped with markers such that their configuration is characteristic of the corresponding instrument. Preferably three markers are arranged on a straight line, the ratio of the distances between them being characteristic for the corresponding instrument. The image processing system may then identify the instruments present in a given projection and provide functionalities for a user that correspond to said instruments. Moreover, the system may be used to locate an instrument of interest in a projection image if the marker configuration of that instrument is known a priori.

20 Claims, 1 Drawing Sheet

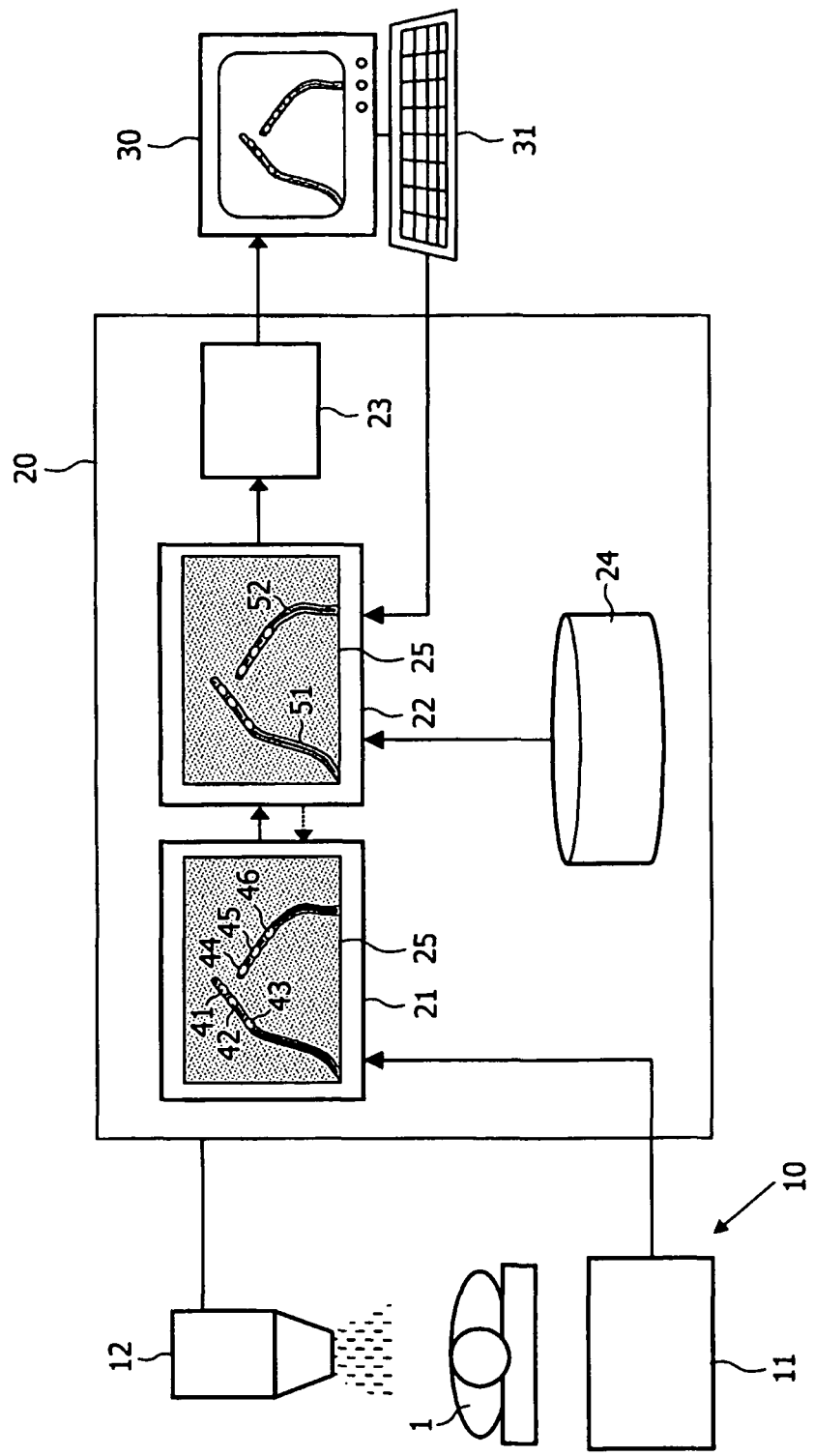

PROCESSING OF IMAGES OF INTERVENTIONAL INSTRUMENTS WITH MARKERS

FIELD OF THE INVENTION

The invention relates to a set of interventional instruments equipped with markers and to an image processing system and a method for the evaluation of projection images of a body volume containing such instruments.

BACKGROUND OF THE INVENTION

An increasing number of surgical interventions is executed with the help of interventional instruments under the control of an imaging system that generates projections of the treated body region. A typical example are interventions in the cardio-vascular system during which often different instruments like (balloon) catheters, guide wires, stents or the like are applied sequentially or simultaneously. Moreover, specific functionalities of the imaging system are provided for different phases of an intervention and for the application of different instruments, wherein these functionalities nowadays must be started manually by a physician.

SUMMARY OF THE INVENTION

Based on this situation it was an object of the present invention to provide means that assist a physician during interventions with several instruments.

This object is achieved by a set of interventional instruments according to claim 1, by an image processing system according to claim 5, and by a method according to claim 10. Preferred embodiments are disclosed in the dependent claims.

According to a first aspect, the invention relates to a set of interventional instruments that may comprise for example catheters, guide wires and endoscopes and instruments of the same type as well as instruments of different types. The instruments shall be equipped with markers that can be detected on projection images of the corresponding instrument, wherein projections of said markers contain features that are characteristic for each instrument. With other words it shall be possible to derive for (nearly) any practically relevant projection direction features from the corresponding projection image of the markers of an instrument that uniquely belong to said instrument. The markers may for example be opaque with respect to X-radiation in order to show up on X-ray exposures with high contrast.

The aforementioned set of interventional instruments has the advantage that each of the instruments can be uniquely identified on a projection image because its markers can be detected on said image and because said markers establish an individual code for the instrument.

According to a first embodiment of the set of instruments, at least some of the instruments have markers with different shapes that can be discriminated on a projection image. The markers may for example have the shape of blobs, crosses or lines which can be identified on an image and serve as a code for the corresponding interventional instrument.

According to a second embodiment, which may be implied alternatively or in parallel to the aforementioned coding by shape, at least two instruments of the set carry three or more markers in a different configuration. The markers themselves may then be identical in shape, for example appear as points or circles on a projection image, because the configuration of the three or more markers on each instrument constitutes its code. The markers are preferably attached to a substantially rigid portion of the corresponding instrument in order to guarantee that their relative spatial arrangement is (approximately) constant. Moreover, the three or more markers are preferably disposed in a line one behind the other, thus guaranteeing that their sequence is invariant with respect to the direction of projection (i.e. the central marker lies in every projection between the other two markers and may thus be uniquely identified). In this case the ratio of the distances between the central marker and the outer markers may be taken as a characteristic value for the corresponding instrument because it remains invariant in all projections.

The invention further relates to an image processing system for the evaluation of projection images of a body volume that may contain at least one interventional instrument of a set of interventional instruments which are equipped with markers, wherein projections of said markers and/or of their configuration shall be characteristic for each instrument. The set of interventional instruments may particularly be one of the embodiments of a set of interventional instruments of the kind described above. The image processing system shall be adapted to:

Detect the markers of interventional instruments on a given projection image that shows a body region with at least one such instrument. Said projection may for example be an X-ray image showing X-ray dense markers.

Identify at least one instrument in said projection image based on the detected markers.

The aforementioned image processing system allows the automatic identification of different instruments of a set of interventional instruments on projection images. The labeling of different instruments with markers is therefore not (only) a visual help for a physician who uses the instruments, but may also be exploited by the image processing system to provide different functions that assist the physician.

The image processing system may preferably comprise a data base in which data about the markers and their configurations are stored for all instruments of the set. With the help of the information in said data base, the image processing system is able to identify any instrument of the given set on a projection image without requiring additional information from the user.

While in the aforementioned embodiment all instruments present in an image are identified with the help of information about all markers on all instruments, the image processing system may also be adapted to localize a specific instrument of interest on a projection image based on given data about the markers and/or their configuration on said instrument. The data may for example be provided explicitly by a user or they may be gained from a previous projection image showing the instrument of interest.

By its definition the image processing system is able to identify at least one instrument on a projection image. According to a preferred embodiment, this information may be used by the image processing system to change its operation mode in dependence on the at least one identified instrument. If the image processing system for example identifies the usage of an instrument related to a specific interventional task, some functionality can be automatically activated, context sensitive menus in the user interface can be enabled, or settings of image processing functionality can be adapted to the properties of the instrument. The possibility to detect a specific kind of instrument in an image can moreover be used for image processing (e.g. for Contrast-to-Noise-Ratio-based setting of acquisition parameters or for stent freeze boost, wherein "stent freeze boost" implies the localization of markers on a stent in image sequences, compensation of movement with the help of the marker positions, and improvement of the visibility of the stent via temporal integration in combination with contrast enhancement) and to automatically distinguish different instruments in the image (e.g. reference and mapping catheter in electrophysiological procedures).

According to another embodiment, the image processing system may be adapted to refine the localization of an instrument with the help of a priori known data about the markers that are carried by said instrument and/or their configuration. If for example the mutual distance between three markers on the instrument is precisely known, this information may be used in order to improve the localization of the markers in the image.

The invention further relates to a method for the evaluation of projection images of a body volume that may contain at least one instrument of a set of interventional instruments. The method comprises the following steps:

Attaching markers to the instruments such that projections of said markers and/or of their configuration are characteristic for each instrument.

Detecting markers in a given projection image.

Identifying at least one instrument in the aforementioned projection image based on the detected markers.

The method comprises in general form the steps that can be executed with an image processing system and a set of interventional instruments of the kind described above. Therefore, reference is made to the preceding description for more information on the details, advantages and improvements of that method.

These and other aspects of the invention will be apparent from and elucidated with reference to the embodiment(s) described hereinafter.

BRIEF DESCRIPTION OF THE DRAWINGS

In the following the invention is described by way of example with the help of the accompanying drawing which schematically shows the use of an image processing system according to the present invention for the identification of different instruments on X-ray projections.

DESCRIPTION OF PREFERRED
EMBODIMENTS

On the left side of the FIGURE, an X-ray imaging system 10 comprising an X-ray tube 12 and an X-ray detector 11 is indicated with which projection images 25 of a body region like the heart of a patient 1 can be generated. The X-ray system 10 is controlled by and its data are received by an image processing system 20. The image processing system 20 is typically realized by a computer (workstation) with conventional components like central processing unit, volatile and nonvolatile memory, I/O interfaces and the like. In the FIGURE, only functional components of the image processing system 20 are shown which will be explained in the following. The FIGURE further depicts a monitor 30 on which images generated by the image processing system 20 can be displayed.

In the US 2003/0209096 A1, the application of tracking systems for the spatial tracking of medical tools like drills that are equipped with markers is described, wherein the three-dimensional position of each marker can be measured. It is mentioned that the markers are positioned in a unique pattern on each tool in order to allow the tracking system to distinguish between said tools. Three-dimensional tracking systems are however in many medical interventions not available. Such interventions (e.g. cardio/vascular) are instead guided by X-ray fluoroscopy. Moreover it can be observed in these cases that increasingly more operating modes and software packages are introduced in order to provide application specific support. A considerable amount of that functionality refers to specific interventional steps and is used in combination with distinct types of interventional devices (e.g. catheters, guide wires).

In order to assist a physician in the aforementioned interventions under X-ray fluoroscopy, it is proposed here to use combinations of X-ray dense markers on the applied interventional instruments that are characteristic for the instrument (or the type of instrument). This approach is illustrated exemplarily in the FIGURE with the help of a projection image 25 generated by the X-ray system 10 during an electrophysiological procedure. The projection 25 contains two instruments 51, 52, for example a reference catheter and a mapping catheter. Each instrument is equipped with two outer markers 41, 43 and 44, 46, respectively, that have a predefined distance from each other, wherein a third marker 42 and 45, respectively, lies in between. The ratio of the distances of the outer markers to the corresponding intermediate marker may then be chosen such that it is unique for each instrument. Thus the ratio of the distances 41-42:42-43 may for example be 1:2, while the ratio of the distances 44-45:45-46 may be 1:1.

In the first "localization module" 21 of the image processing system 20, all markers 41, 42, 43, 44, 45, 46 are localized on the projection image 25 with the help of standard algorithms of image processing. In the following "identification module" 22, this information is then used to identify the specific instruments present in the projection image 25. This identification may be done with the help of a data base 24 in which the marker positions (or at least characteristic values like the aforementioned ratios) are stored for a given set of interventional instruments. In more detail, the identification procedure might comprise the following steps:

Searching for triple marker combinations lying (approximately) on a line with a predefined maximum distance from each other (said maximum distance corresponding to the real distance of the outermost markers, for example 41, 43, from each other).

Calculating for each found triple marker combination the ratio of the distances of the outermost markers to the corresponding intermediate marker, i.e. the quotients $R_{51}$=41-42:42-43 and $R_{52}$=44-45:45-46.

Identifying the object to which the triple markers belong as a certain instrument if the calculated ratio corresponds (within predefined tolerances) to a value stored in the data base 24 for said instrument. Thus a ratio of about 1:1 would be associated with the reference catheter 52, while a ratio of about 1:2 (or 2:1) would be associated with the mapping catheter 51.

The information obtained in modules 21, 22 may be used by a further module 23 in order to provide functionalities that are specific for the detected instruments 51, 52. For example context sensitive menus or specific image processing algorithms like stent freeze boost may be provided. The projection 25 may moreover be displayed on the monitor 30, wherein the identification result may for example be indicated by different colors or by labels.

As is indicated by a broken line in the FIGURE, the processing of the localization module 21 and the identification module 22 may be interrelated such that the result of the identification procedure in module 22 is used for a refined localization of the markers 41-46 on the projection 25 in module 21. Thus the exactly known distance between the markers 41, 42, 43 on the instrument 51 may for example be used in order to correct the measured positions of these markers.

While the described application of the image processing system 20 is based on the identification of all instruments 51, 52 that are present in a given projection 25 with the help of the data base 24, the individual marking of interventional instruments may also be used for the localization of a specific type of instrument in a projection. In this case, the localization module 21 works as described above, i.e. the positions of the markers 41-46 are first determined in the projection 25. In the identification module 22, not every present instrument is identified, but a specific instrument of interest is particularly looked for. Which instrument is looked for may for example be selected or defined with corresponding marker parameters that are entered by a user via a keyboard 31 or a similar input device. Thus a user would for example input a desired distance ratio of 2:1 if the mapping catheter 51 shall be localized.

In the next step, the instrument of interest is identified and localized in the projection image 25 by module 22 (i.e. it is checked if the instrument is present and, if it is, where) by looking for marker combinations with the required features. In general, a model based approach facilitates marker detection. The marker configuration of the instrument that is looked for may also be provided from a previous automatic instrument identification step. Thus, the data base 24 is not necessarily used during the localization of a specific instrument in a projection image.

In general, using more markers can increase robustness of identification and localization. Furthermore, different kinds of markers (blobs, crosses, short lines) can be used, which can further increase robustness and the number of instruments that can be distinguished.

Finally it is pointed out that in the present application the term "comprising" does not exclude other elements or steps, that "a" or "an" does not exclude a plurality, and that a single processor or other unit may fulfill the functions of several means. Moreover, reference signs in the claims shall not be construed as limiting their scope.

The invention claimed is:

1. An image processing system for evaluation of projection images of a body volume including at least one instrument of a plurality of interventional instruments, the image processing system comprising:
   a plurality of markers affixed to each of the plurality of instruments in a configuration that provides a ratio of distances between the markers characteristic of an instrument on which the markers are affixed; and
   a processor configured to
      detect the markers of the at least one of the plurality of instruments on a projection image;
      identify uniquely which ones of the plurality of instruments corresponds to the at least one instrument in the projection image from the ratio of distances between the detected markers; and
      change an operating mode of the image processing system automatically in dependence on which of the plurality of instruments is uniquely identified in the projection image.

2. The image processing system according to claim 1, wherein at least some markers comprise different shapes that can be discriminated on the projection image.

3. The image processing system according to claim 1, wherein at least two of the instruments carry three or more markers that are attached to said instruments in different configurations.

4. The image processing system according to claim 1, wherein the markers are opaque with respect to X-radiation.

5. The image processing system according to claim 1, comprising a data base in which data about the markers and their configurations is stored for the plurality of instruments.

6. The image processing system according to claim 5, wherein the image processing system is adapted to localize an instrument of interest on the projection image from the data about the markers and/or their configuration for said instrument and identifying data supplied by a user related to the instrument of interest.

7. The image processing system according to claim 1, wherein the image processing system is adapted to provide operations of the image processing system that are specific for the identified at least one instrument in the projection image.

8. The image processing system according to claim 5, wherein the image processing system is adapted to refine the localization of an instrument with the help of the data about the markers and/or their configuration for said instrument.

9. The image processing system according to claim 1, wherein the plurality of markers on at least two of the instruments comprise three or more markers that are attached to said instruments in a substantially straight line.

10. The image processing system according to claim 9, wherein the at least one instrument in the projection image is identified from a ratio of distances between the three or more markers including intermediate markers that include other markers on each direction of the substantially straight line and outside markers that include other markers only in one direction of the substantially straight line.

11. The image processing system according to claim 10, wherein the at least one instrument in the projection image is identified from a ratio of distances between outside markers and intermediate markers.

12. The image processing system according to claim 1, wherein the processor is configured to indicate the unique identification in the projection image.

13. The image processing system according to claim 1, wherein the processor is configured to indicate the unique identification in the projection image by different colors or labels.

14. The image processing system according to claim 1, wherein the processor is configured to distinguish different instruments in the projection image based on which of the plurality of instruments is identified in the projection image.

15. A method for evaluation by an image processing system of projection images of a body volume including at least one instrument of a plurality of interventional instruments, the method comprising acts of:
   attaching a plurality of markers to each of the plurality of instruments in a configuration that provides a ratio of distances between the markers characteristic of the instrument on which the markers are affixed;
   detecting the markers of the at least one of the plurality of instruments in a projection image;
   identifying uniquely which ones of the plurality of instruments corresponds to the at least one instrument in said projection image from the ratio of distances between the detected markers; and
   automatically activating a specific image processing functionality in dependence on which of the plurality of instruments is identified in said projection image.

16. An image processing system for evaluation of projection images of a body volume including at least one instrument of a plurality of interventional instruments, the image processing system comprising:

a plurality of markers affixed to each of the plurality of instruments in a configuration that provides a ratio of distances between the markers characteristic of an instrument on which the markers are affixed; and a processor configured to
- detect the markers of the at least one of the plurality of instruments on a projection image;
- identify uniquely which ones of the plurality of instruments corresponds to the at least one instrument in the projection image from the ratio of distances between the detected markers; and
- indicate the unique identification in the projection image.

17. The image processing system according to claim 16, wherein the processor is configured to indicate the unique identification in the projection image by different colors or labels.

18. The image processing system according to claim 16, comprising a data base in which data about the markers and their configurations is stored for the plurality of instruments.

19. The image processing system according to claim 16, wherein the processor is configured to change the operating mode of the image processing system by automatically enabling a context sensitive menu in the user interface in dependence on which of the plurality of instruments is uniquely identified in the projection image.

20. The image processing system according to claim 16, wherein the processor is configured to change the operating mode of the image processing system by automatically adapting settings of image processing functionality in dependence on which of the plurality of instruments is uniquely identified in the projection image.

* * * * *